US012560584B2

(12) United States Patent
Rasulov et al.

(10) Patent No.: US 12,560,584 B2
(45) Date of Patent: Feb. 24, 2026

(54) METHOD AND APPARATUS FOR ASSESSING GAS EXCHANGE OF PLANTS

(71) Applicant: University of Tartu, Tartu (EE)

(72) Inventors: Bakhtier Rasulov, Tartu (EE); Roman Leinus, Tartu (EE); Hannes Kollist, Tartu (EE)

(73) Assignee: UNIVERSITY OF TARTU, Tartu (EE)

( * ) Notice: Subject to any disclaimer, the term of this patent is extended or adjusted under 35 U.S.C. 154(b) by 372 days.

(21) Appl. No.: 18/021,964

(22) PCT Filed: Aug. 19, 2021

(86) PCT No.: PCT/EP2021/073089
    § 371 (c)(1),
    (2) Date: Feb. 17, 2023

(87) PCT Pub. No.: WO2022/038246
    PCT Pub. Date: Feb. 24, 2022

(65) Prior Publication Data
    US 2023/0349878 A1     Nov. 2, 2023

(30) Foreign Application Priority Data

Aug. 19, 2020    (GB) ...................................... 2012952

(51) Int. Cl.
    *G01N 33/00*        (2006.01)
    *G01N 1/24*         (2006.01)
(52) U.S. Cl.
    CPC ........... *G01N 33/0098* (2013.01); *G01N 1/24* (2013.01); *G01N 2001/241* (2013.01)
(58) Field of Classification Search
    CPC ................ G01N 33/0098; G01N 1/24; G01N 2001/241; G01N 2021/635;
        (Continued)

(56) References Cited

U.S. PATENT DOCUMENTS 3,613,308 A    10/1971   Klein et al.
4,768,390 A    9/1988    Baker et al.
                (Continued)

FOREIGN PATENT DOCUMENTS

CN    107709972 A  *  2/2018  ......... G01N 21/3504
CN    109174017 A  *  1/2019  ............. B01D 53/02
                (Continued)

OTHER PUBLICATIONS

Faralli, et al., "Natural genetic variation in photosynthesis: an untapped resource to increase crop yield potential?", The Plant Journal, 101, pp. 518-528 (2020).
                (Continued)

*Primary Examiner* — Robert R Raevis
(74) *Attorney, Agent, or Firm* — Lippes Mathias LLP

(57)             ABSTRACT

A method and apparatus are disclosed for assessing gas exchange of plants. The method includes receiving in a gas analyzer a plurality of test air samples from a leaf chamber corresponding respectively to first and second plant leaf samples received separately and in sequence in the leaf chamber while being exposed to light to form the first and second test air samples, the first and second test air samples being received in sequence in the gas analyzer as an integrated gas stream, and the gas analyzer analyzing the integrated gas stream as it flows therethrough. The measuring apparatus includes a leaf chamber for receiving therein a plant leaf sample to be tested, a pump communicating with the leaf chamber for supplying air thereto, and an analyzer communicating with the leaf chamber for receiving air therefrom and for analyzing the air received.

19 Claims, 4 Drawing Sheets

(58) Field of Classification Search

CPC .. G01N 2021/8466; A01G 7/00; A01G 25/16; A01G 7/02; A01G 9/18

USPC ......... 73/1.06, 19.01, 23.2, 31.01–31.3, 863, 73/863.01, 864.33, 864.34, 864.81, 73/864.91, 866, 432.1

See application file for complete search history.

(56) References Cited

U.S. PATENT DOCUMENTS

| | | | |
|---|---|---|---|
| 10,379,039 B2 | 8/2019 | Tanaka et al. | |
| 2012/0073355 A1 | 3/2012 | Johnson et al. | |
| 2018/0136184 A1* | 5/2018 | Morgan | G01N 33/0067 |

FOREIGN PATENT DOCUMENTS

| | | |
|---|---|---|
| EP | 0209247 A1 | 10/1987 |
| EP | 3312587 A1 | 4/2018 |

OTHER PUBLICATIONS

Stinziano, et al., "The rapid A—$C_i$ response: photosynthesis in the phenomic era," Plant, Cell Environ. 40:1256-1262 (2017).

Yonemura, et al., "A high-performance system of multiple gas-exchange chambers with a laser spectrometer to estimate leaf photosynthesis, stomatal conductance, and mesophyll conductance," Journal of Plant Research, Tokyo, JP, vol. 132, No. 5, pp. 705-718 (Jul. 2019) (Abstract Only).

Bio-Science Inc., Instruction Manual for CI-340 Handheld Photosynthesis System, CID, 2013, available at https://www.cid-inc.com/plant-science-tools/photosynthesis-measurement/ci-340-handheld-photosynthesis-system/?gclid=CjwKCAiA9v0ABhBfEiwATCi7GOglehyztoSt3-iboa0ASYL52LYSx2u8pOjKtt8caMizTh7Q5FwrRoCNvgQAvDBwE, 81 pages (2013).

LI-COR Inc., "LI-6800 Portable Photosynthesis System," archived at https://web.archive.org/web/20200425230212/https:/www.licor.com/env/products/photosynthesis/LI-6800/ on Apr. 25, 2020.

Operation Manual for "CI-340 Handheld Photosynthesis System"; CID Bio-Science, Inc.; Nov. 1, 2011, 81 pages.

* cited by examiner

METHOD AND APPARATUS FOR ASSESSING GAS EXCHANGE OF PLANTS

METHOD AND APPARATUS FOR ASSESSING GAS EXCHANGE OF PLANTS

This application claims the priority of International Application PCT/EP2021/073089, filed Aug. 19, 2021, and claims priority from GB 2012952.4, filed Aug. 19, 2020, from which the PCT application claims priority, the disclosures of which are incorporated herein by reference in their entireties.

BACKGROUND

The invention relates to a method and apparatus for assessing gas exchange of plants.

To breed and select new plant varieties that can cope with environmental stresses caused by climate change, tools are needed to assess physiological functions of plants in the field. Such information is needed for screening desired gas exchange traits in plants in the field. The information can assist the development of plant varieties with improved photosynthetic characteristics and efficient use of water in order to provide food and fiber for mankind.

Several companies produce gas-analysis systems for measuring photosynthesis and transpiration. These include Licor Environmental, Heinz Walz GmbH and PP Systems. Devices produced by these companies allow accurate measurement of several plant photosynthetic traits such as: net $CO_2$ assimilation rates $A_{net}$, with a typical measurement time 1 to 5 min; photosynthetic light response curves, with a typical measurement time 10 to 30 min; and photosynthetic $CO_2$ response curves, with a typical measurement time 10 to 60 min. These measurements are usually done by clamping part of the leaf into an infrared gas exchange analysis system. Even though these systems produce valuable information relating to the physiological status of plant leaves, their throughput is relatively low.

Several studies have indicated poor correlation between net $CO_2$ assimilation rate, $A_{net}$ and yield (see "Natural genetic variation in photosynthesis: an untapped resource to increase crop yield potential?" by Faralli and Lawson, The Plant Journal (2020) 101, 518-528 2020 published by the Society for Experimental Biology, and references therein). This is not surprising as analyses are often based on either measuring maximal photosynthetic capacity (e.g., $A/C_i$ and $A/Q$ curves, where $C_i$ denotes intracellular $CO_2$ concentration and Q light intensity) that are not realized in the field or instantaneous measurements that represent a single leaf measurement of A that fails to characterize the diurnal photosynthetic pattern of a plant community.

BRIEF DESCRIPTION

Viewed from one aspect, the invention provides a method for assessing gas exchange of plants, comprising receiving in a gas analyzer a plurality of test air samples from a leaf chamber each corresponding to a respective one of a plurality of plant leaf samples received separately and in sequence in the leaf chamber while being exposed to light to form the plurality of test air samples, the plurality of test air samples being received in sequence in the gas analyzer as an integrated gas stream, and the gas analyzer analyzing the integrated gas stream as it flows therethrough.

Viewed from another aspect the invention provides apparatus for assessing gas exchange of plants, comprising a leaf chamber configured to receive a plurality of plant leaf samples separately and sequentially therein and to expose the plant leaf samples to light while passing air through the leaf chamber to form a corresponding plurality of test air samples, the leaf chamber being openable for removal of the plurality of plant leaf samples therefrom and for receiving therein a next plant leaf sample of the plurality thereof, and a gas analyzer configured to receive from the leaf chamber the plurality of test air samples in sequence as an integrated gas stream and to analyze the integrated gas stream as it flows therethrough.

Such a method and apparatus can quickly carry out analysis of the test air samples from the plant leaf samples in sequence because the plurality of test air samples pass in sequence to the analyzer as an integrated gas stream. Any delay in carrying out the analysis may be minimized. Therefore, plural sequential measurements may be carried out in a relatively short period of time. There is no need to interrupt the gas stream between leaf tests. Such interruption is done in prior art systems to purge the leaf chamber, any line between the leaf chamber and the analyzer, and the analyzer.

For example, by the analyzer analyzing an integrated gas stream from several plant leaves, for example 10 or more, or 20 or more, or 30 or more, plant leaf samples, the analysis can very accurately reflect the photosynthesis of the plant community. This can be done effectively based on a principle of many samples producing an integrated gas stream.

The plurality of test air samples may comprise at least 10 test air samples. There may be 20 or more, or 30 or more test air samples, each corresponding to a respective plant leaf sample.

In embodiments, the plurality of test air samples forms an integrated gas stream, in that they flow together to the gas analyser in a row and at the same rate. This can be the case even if the flow stops, for example when the leaf chamber is opened.

Each plant leaf sample may be an entire leaf, or it may be part of a leaf.

In general, in known systems, measuring plant photosynthesis and transpiration are based on the principle: one sample/leaf—one measurement. Usually, part of the plant leaf is clamped to the gas exchange chamber to measure its gas exchange. In order to get the gas exchange result of one leaf, it is necessary to analyze the gas passing through the chamber in the volume necessary for filling the entire measurement path 3 times, to ensure accuracy. This is because once the leaf has been placed in the chamber, the composition of the gas reaching the gas analyzer does not change immediately to reflect the gas exchange result of the leaf, until the gas in the measurement path has been purged of the previously present gas. The measurement path includes the leaf chamber, the volume of the pipeline from the leaf chamber to the gas analyzer, and the volume of the gas analyzer and its components. Thus, the measurement time depends on the speed of the air flow in the chamber and the volume of the measuring path. The air flow rate cannot be arbitrarily increased to high values, since this would lead to a loss of signal. An increase in the area of the leaf surface, which allows a larger signal to be obtained, is in most cases limited by the morphological features of the analyzed leaves. Therefore, modern plant gas-analysis systems for measuring photosynthesis and transpiration operate on the principle of one sample—one measurement, and have a minimum measurement time of one sample of about 20 seconds, in reality several minutes.

In such known systems, measurement time can be minimized by reduction of the volume of the measuring cuvette of the gas analyzer. However, a decrease in the volume of the analysis cuvette almost proportionally reduces the sensitivity of the measuring device and greatly reduces (by several times) the accuracy of the measurements. Moreover, even a 20 second measurement time does not guarantee the absence of the so-called "chamber effect" on the status of the measured leaf. Therefore, in order to obtain a correct measurement, the leaf is allowed to adapt for some time to the conditions of the measurement cuvette, which further increases the measurement time. Typically, such systems are used to obtain information for the kinetic parameters of a leaf by measuring the light, carbon dioxide, and temperature response curves on photosynthesis and transpiration as described above. However, such systems are not able to provide information on the actual values of photosynthesis and transpiration in the field, and even more those devices are not suitable for measuring these physiological parameters across plant communities.

To measure photosynthesis and transpiration across plant communities, as described herein, it is beneficial to measure one plant leaf sample quickly (about 5-7 seconds) and it is useful to be able to obtain values for tens or hundreds of leaves in one plot, height, developmental stage et cetera.

The method of the invention may comprise enclosing a first plant leaf sample of the plurality of plant leaf samples in the leaf chamber, passing air through the leaf chamber while exposing the first plant leaf sample to light so as to form a first test air sample of the plurality of test air samples, passing the first test air sample to the gas analyzer, opening the leaf chamber, removing the first plant leaf sample therefrom, enclosing a second plant leaf sample of the plurality of plant leaf samples in the leaf chamber, passing air through the leaf chamber while exposing the second plant leaf sample to light so as to form a second test air sample of the plurality of test air samples, passing the second test air sample to the gas analyzer, and removing the second plant leaf sample from the leaf chamber. These steps may be repeated with further plant leaf samples of the plurality thereof mentioned above.

The gas analyzer may analyze the integrated gas stream as it flows therethrough to produce analysis data.

The method may comprise receiving analysis data from the gas analyzer, processing the analysis data to produce a test result for each of the plant leaf samples, and combining the test results for the plant leaf samples to generate an average test result for the plant leaf samples. The apparatus may comprise a data processor configured to receive analysis data from the gas analyzer, to process the analysis data to produce a test result for each of the plant leaf samples, and to combine the test results for the plant leaf samples to generate an average test result for the plant leaf samples.

A test result may be produced for each of the plurality of plant leaf samples, wherein said plurality of test air samples comprises at least 10 test air samples (or at least 20 or 30 test air samples), and the test results for the plurality of plant leaf samples may be combined to generate an average test result for that plurality.

An average test result can reflect the status of plural plant leaf samples, for example an average result for plural leaves of a single plant at a single level in the canopy, or an average test result for plural leaves of a single plant at different levels in the canopy, or an average test result for plural leaves of different plants at a single or different levels in the canopy, as desired. Such an average test result is useful for assessing the photosynthetic activity and water transpiration reflecting the physiological status of plants in the community.

The analysis data produced by the gas analyzer may be in the form of signal points. There may be a set of signal points sequenced over time corresponding to each test air sample.

The analysis data received from the gas analyzer may comprise a plurality of sets of signal points sequenced over time, each set of signal points corresponding to a respective test air sample of the plurality thereof. The method may comprise combining the sets of signal points to generate the average test result for the plurality of plant leaf samples.

The apparatus may comprise the gas analyzer being configured to analyze the gas stream to produce a plurality of sets of signal points sequenced over time, each set of signal points corresponding respectively to a respective test air sample of the plurality thereof. The data processor may be configured to combine the sets of signal points to generate the average test result for the plurality of plant leaf samples.

Thus, an average test result may be determined to assess the gas exchange of the plurality of plant leaf samples, e.g., the plant leaf samples of the plurality thereof when the plurality is at least 10.

Each of the test air samples received in the gas analyzer may comprise a leading part in the flow direction, an intermediate part upstream of the leading part, and a trailing part upstream of the intermediate part. The method may comprise processing the signal points of the sets thereof which correspond to the intermediate parts of the test air samples to produce said test result for each of the plurality of plant leaf air samples.

The data processor of the apparatus may be configured to process the signal points of the sets thereof which correspond to the intermediate parts of the test air samples to produce said test result for each of the plurality of plant leaf samples.

In embodiments, the leading part of a given test air sample will be adjacent to a portion of ambient air which enters the chamber when it is opened to receive the corresponding plant leaf sample, and similarly the trailing part of the test air sample will be adjacent to a portion of ambient air which enters the chamber when it is opened to remove the corresponding plant leaf sample. Therefore, by using the signal points of the sets thereof which correspond to the intermediate parts of the test air samples, this will generally not have been affected by diffusion from any ambient air which has entered the system. An accurate test result can be produced for each test air sample.

In an embodiment, the gas analyzer measures the gas over a period of time, for example 0.5 seconds, to produce each signal point. A plurality of such signal points are produced for each test air sample over a period of time corresponding to the same period of time over which the plant leaf sample is enclosed in the chamber and exposed to light, for example 14 signal points in the case of a seven second exposure period. Of that plurality of signal points one or more of the earliest ones corresponding to the leading part of the test air sample, and one or more of the latest ones corresponding to the trailing part of the test air sample, are not used in producing the analysis data, in view of the potential diffusion of ambient air affecting those signal points. Rather, the signal points corresponding to the intermediate part of the test air sample are used to generate the average test result.

The method may comprise allowing an air flow into the leaf chamber to form the test air samples. The apparatus may have a flow control valve for allowing the air flow into the leaf chamber. The airflow may be generated by a source of pressurised air such as a pump. The flow control valve may be opened by a system controller when the leaf chamber is closed.

In order to ensure that each plant leaf sample is exposed to the airflow for the same measurement time, the flow control valve may be closed by the system controller when a measurement time has elapsed since the valve was opened. An operator may be alerted to the fact that the measurement time is complete by a visual and/or audible alert. This allows the leaf chamber to be opened for removal of the plant leaf sample and the insertion of another plant leaf sample.

The method may comprise sensing when the leaf chamber is open or closed. Thus, the apparatus may comprise a sensor for sensing when the leaf chamber is open or closed. This can ensure that at least during testing air flow can only occur when the leaf chamber is closed. If the leaf chamber is opened during airflow, inadvertently or otherwise, the system controller can close the flow control valve in response to a signal from the sensor indicating that the leaf chamber is open.

The system controller may receive signals from the sensor and output instructions to open or close the flow control valve.

The method may comprise allowing reference air to flow through the leaf chamber when empty, before a first of the plurality of plant leaf samples has been received in the leaf chamber, and the gas analyzer analyzing the reference air. This can allow concentrations of gases in the reference air to be determined when no plant sample is present. The gas analyzer can produce a reference signal. Therefore, by using the same reference air when a plant leaf sample is present in the leaf chamber, changes in gas concentrations relative to the reference air, which are caused by plant gas exchange activity, can be determined.

The reference air may be obtained from a single source of reference air. The air flow into the leaf chamber to form the test air samples may also be obtained from the single source of reference air. By having a single source of reference air the concentrations of gases in the reference air will be the same when it is analyzed as when the reference air is passed to the leaf chamber with the respective plant leaf samples received therein. The concentrations of gases, namely of $CO_2$ and $H_2O$, will be modified as the reference air passes through the leaf chamber by the photosynthetic activity of the respective plant leaf sample present in the leaf chamber to produce the respective test air sample.

The reference air may be derived from a single charge thereof in a pump. Thus, the apparatus may comprise a pump configured to be filled with a single charge of air and sequentially to supply plural doses of air from the single charge each for passing to the leaf chamber.

The pump may have a flexible air intake pipe. This allows an inlet to the intake pipe to be set away from people and other potential sources of $CO_2/H_2O$ when the pump is being filled with reference air.

The reference air may be unprocessed ambient air. In known methods, standardized air is created by removing gases and then adding them precisely to required concentrations. By using reference air, which is unprocessed ambient air, the use of such relatively complicated equipment is not necessary. Moreover, if the ambient air is taken from the vicinity of the plant the leaves of which are being analyzed, this can produce a good representation of the gas exchange of a plant in the field.

Each plant leaf sample may be received in the leaf chamber for a period of 15 seconds or less.

This measurement time is a much shorter period of time for generating a test air sample than in the known gas exchange measurement methods, which typically involve measurement times of 1 to 5 minutes. However, the physiological properties of the leaf may change after 20 seconds in the leaf chamber. In embodiments, each leaf sample may be enclosed in the leaf chamber for 10 seconds or less, for example for a period of time between 5 and 10 seconds, or between 6 and 8 seconds. By obtaining a test air sample from a leaf in such relatively short periods, several leaves can be tested in sequence very quickly.

The apparatus may be portable. It can be carried by one person in a back pack for example, enabling the collection of data in the field.

The pump may be connected to the leaf chamber by a flexible conduit. The use of a flexible conduit allows the pump and the leaf chamber, which may be part of a leaf chamber module, to be separate whilst being connected by the flexible conduit. This facilitates positioning the leaf chamber in the field to receive plant leaf samples without having to maneuver the pump. For example the leaf chamber may be part of a hand held leaf chamber module, whilst the pump can be separately carried, such as in a backpack.

The leaf chamber may be connected to the gas analyzer by a flexible conduit along which the integrated gas stream flows. Thus, there may be a first flexible conduit connecting the pump to the leaf chamber and a second flexible conduit connecting the leaf chamber to the gas analyzer. The use of a flexible conduit between the leaf chamber and the gas analyzer allows the leaf chamber, which may be part of a leaf chamber module, and the gas analyzer to be separate whilst being connected by the flexible conduit. This facilitates positioning the leaf chamber in the field to receive plant leaf samples without having to maneuver the gas analyzer. For example, the leaf chamber may be part of a hand held leaf chamber module, whilst the gas analyzer can be separately carried, such as in a backpack. The pump and the gas analyzer may be provided together in a single portable container such as a backpack.

In another aspect the invention provides apparatus for assessing gas exchange of plants, comprising a gas analyzer and means adapted to execute the steps of the methods described herein.

The invention also provides a computer program comprising instructions to cause such apparatus to execute the steps of the methods described herein.

The invention also provides a non-transitory computer-readable medium having stored thereon such a computer program.

In a further aspect the invention provides measuring apparatus for assessing gas exchange of plants, comprising a leaf chamber for receiving therein a plant leaf sample to be tested, a pump communicating with the leaf chamber for supplying air thereto, an analyzer communicating with the leaf chamber for receiving air therefrom and for analyzing the air received, wherein the pump is configured to be filled with a single charge of air and to supply plural doses of air from that single charge each for sequentially testing a respective plant leaf sample of a plurality of plant leaf samples.

By using a pump which supplies plural doses from a single charge of air, air with the same concentration of gases (in particular, carbon dioxide and water vapour) can be used for plural tests. This means that plural plant leaf samples can be tested using air with the same reference gas concentrations. There is no need to employ devices for creating standardized air. An analysis of the air from the single charge without the presence of a plant leaf sample can be used to establish the reference gas concentrations.

The pump may have the features discussed herein in relation to other aspects of the invention.

The pump can be used to collect ambient air with the same carbon dioxide and water vapour concentrations from the immediate neighbourhood of a plant to be analyzed. For example, such a collection may take place at a certain level in a plant canopy, and then plant leaf samples may be selected at that same level for analysis. A flexible air intake pipe as described earlier may be used.

A suitable pump for being configured to be filled with a single charge of air is a positive displacement pump. This can trap the single charge in a cavity and then discharge under pressure doses from that single charge.

In an embodiment, the pump is a bellows pump comprising a bellows and a weight for applying pressure to the bellows to discharge air. Such a bellows pump does not need electricity to function and can create a constant airflow, i.e., avoiding pulsations.

The measuring apparatus may comprise a first one-way valve in an inlet path allowing the pump to be filled and a second one-way valve in an outlet path allowing discharge of air from the pump.

When it is desired to fill the pump with the single charge of air, this can be done via the inlet path and allowed by the first one-way valve while the second one-way valve prevents air from being drawn into the pump via the outlet path. Similarly, when it is desired to supply doses of air from the pump, this is done via the outlet path and allowed by the second one-way valve while the first one-way valve prevents escape of air via the inlet path.

The measuring apparatus may comprise a flow control valve upstream of the leaf chamber for controlling flow of air into the leaf chamber.

When sequentially testing respective plant leaf samples from a plurality thereof, the leaf chamber has to be opened to receive a plant leaf sample and then closed again. When the leaf chamber is open, the flow control valve can be closed to stop flow of air from the pump into the leaf chamber. Once the plant leaf sample is in the chamber the flow control valve can be opened to allow the flow of air, in order to deliver a dose of air to that sample. The flow control valve can be closed in response to a signal from a system controller when a measurement time has elapsed. The opening and closing can be sensed by a sensor which sends signals to the system controller. The flow control valve may be a solenoid valve.

BRIEF DESCRIPTION OF THE DRAWINGS

Certain preferred embodiments of the invention will now be described by way of example and with reference to the accompanying drawings, in which.

DETAILED DESCRIPTION

Figure 1:
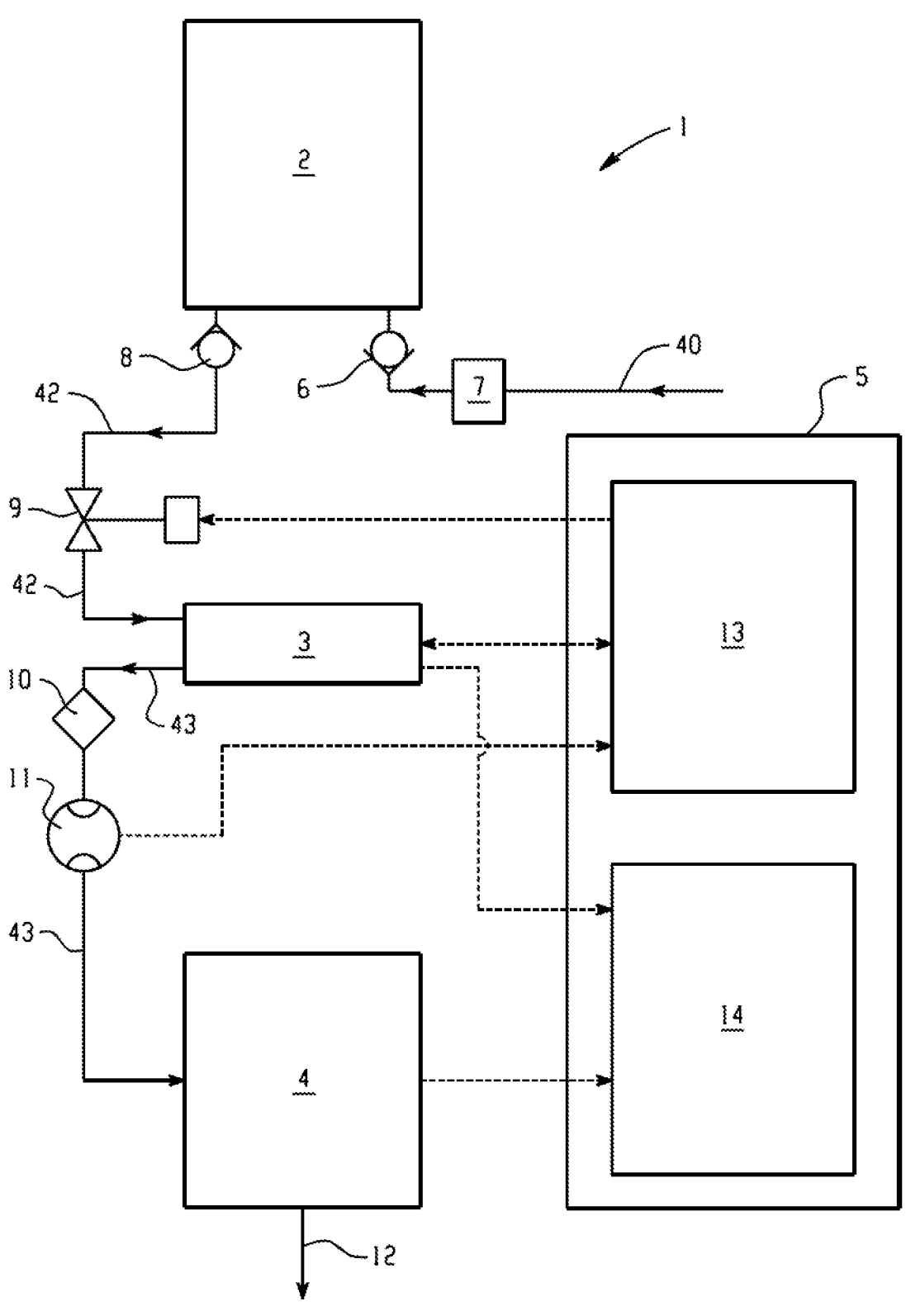
FIG. 1 is a schematic view or apparatus for assessing gas exchange of plants.

Referring to FIG. 1, this shows apparatus 1 for assessing gas exchange of plants, comprising a pump 2, a leaf chamber module 3, a gas analyzer 4 and a computing unit 5.

In FIG. 1, solid arrows show air flow through the system, and dotted arrows show signals sent between components of the system.

The pump has a first one-way valve 6 to which an air intake pipe 40 is connected to provide an inlet path allowing the pump to be filled. An air filter 7 is provided in the air intake pipe 40 upstream of the one-way valve 6.

The pump has an outlet path and a second one-way valve 8 in the outlet path allowing discharge of air from the pump. A first flow conduit 42 extends between the pump and the leaf chamber module 3. A flow control valve in the form of a solenoid valve 9 is provided in the first flow conduit 42 downstream of the second one-way valve 8 in order to control airflow from the pump to the leaf chamber module 3.

The leaf chamber module 3 has an inlet to allow air to flow into the module and an outlet for air to flow out of the module. A second flow conduit 43 extends between the leaf chamber module and the gas analyzer 4. A dust filter 10 is provided in the second flow conduit 43 downstream of the leaf chamber module 3 to filter air which has been exposed to a plant leaf sample. A flow meter 11 is provided in the second flow conduit 43 downstream of the dust filter and upstream of the gas analyzer 4.

The first and second conduits 42 and 43 comprise flexible pipes in this embodiment. This means that the pump 2 and the gas analyzer 4 can be carried at a spacing from the leaf chamber module 3, allowing this to be hand held and easily maneuverable while the pump and the gas analyzer can be separately carried by a user, for example in a back pack. This facilitates use in the field.

The gas analyzer 4 has an outlet path 12 for the escape of gas which has been analyzed.

The computing unit 5 consists of a system controller 13 and a data processing and logging unit 14. The system controller 13 is connected to the solenoid valve 9 so that the system controller can control the valve to switch on or off airflow as required. The leaf chamber module 3 is connected to the system controller 13 so that the leaf chamber module can send signals to the system controller to indicate whether a leaf chamber of the leaf chamber module is open or closed. This allows the system controller to control the solenoid valve 9 to switch off the airflow from the pump to the leaf chamber when the leaf chamber is open, and to switch on the airflow when the leaf chamber is closed.

The leaf chamber module 3 is connected to the data processing and logging unit 14 so that it can send signals to the unit relating to the light intensity to which a plant leaf sample is exposed and relating to the temperature of the plant leaf sample.

The flow meter 11 is connected to the system controller 13 so that it can send signals to the system controller to indicate the airflow rate from the leaf chamber module 3 to the gas analyzer 4. This can act as a check by the system controller that when the solenoid valve 9 is closed to airflow, the airflow through the flow meter 11 stops.

The gas analyzer 4 is connected to the data processing and logging unit 14 so that it can send signals to the unit 14 indicative of the concentrations of gases determined in the gas analyzer.

Figure 2C:
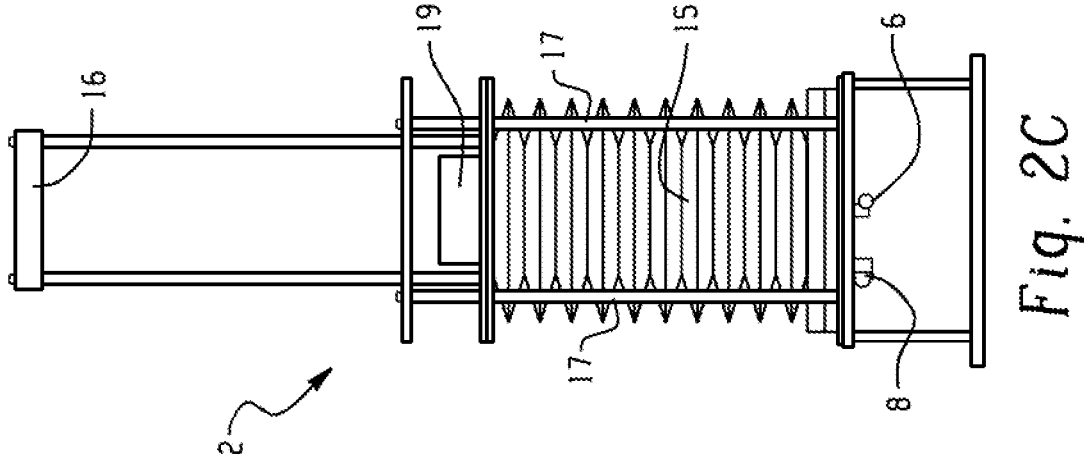
FIG. 2C is an elevation view of the pump with the bellows in an expanded condition.
Figure 2B:
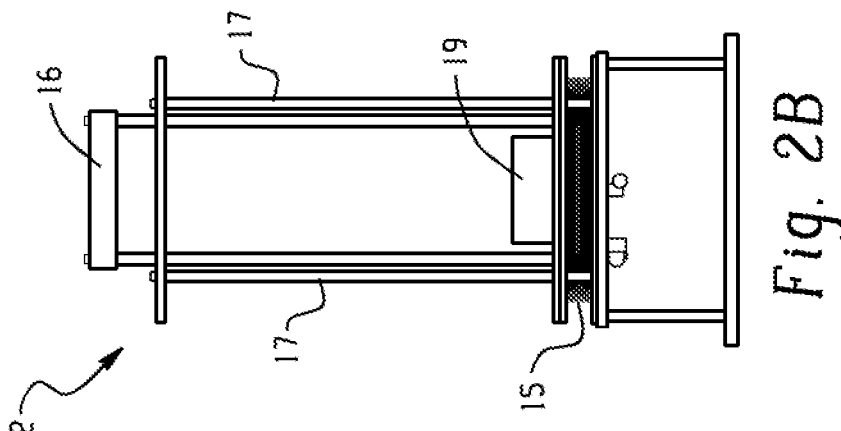
FIG. 2B is an elevation view of the pump with its bellows in a collapsed condition.
Figure 2A:
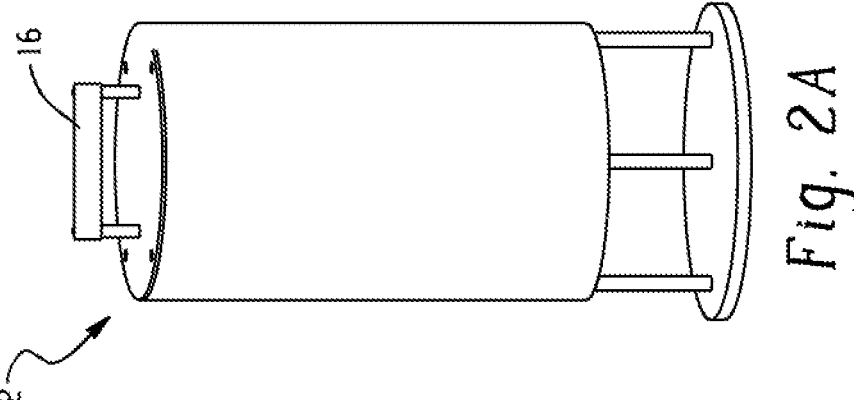
FIG. 2A is a perspective view of a pump of the apparatus.

Further details of the pump 2 are shown in FIGS. 2A, 2B and 2C. The pump has a bellows 15 which can be expanded by a pull handle 16. This allows air to enter the bellows via the first one-way valve 6, with the air filtered by the air filter 7 upstream of the valve. The pump has a pair of vertical guide rods 17 for guiding a pressure plate 18 disposed on the bellows 15 in an up and down path. A weight 19 is located on the pressure plate 18 to cause the plate to exert pressure on the bellows, so that in use providing the solenoid valve 9 is open air flows under pressure via the second one-way valve 8 in the outlet path allowing discharge of air from the pump. The air flows through the dust filter 10 and the flow meter 11 to the gas analyzer 4.

In use, by pulling the pull handle 16 the bellows 15 is expanded and filled with a single charge of air. When the solenoid valve 9 is opened a dose of air from that single charge is delivered to the leaf chamber module 3. When the valve is closed the flow of air out of the pump and to the leaf chamber module is interrupted. The pump is configured to be filled with a single charge of air and to supply plural doses of air from single charge each for sequentially testing a respective plant leaf sample of a plurality of plant leaf samples.

Figure 3:
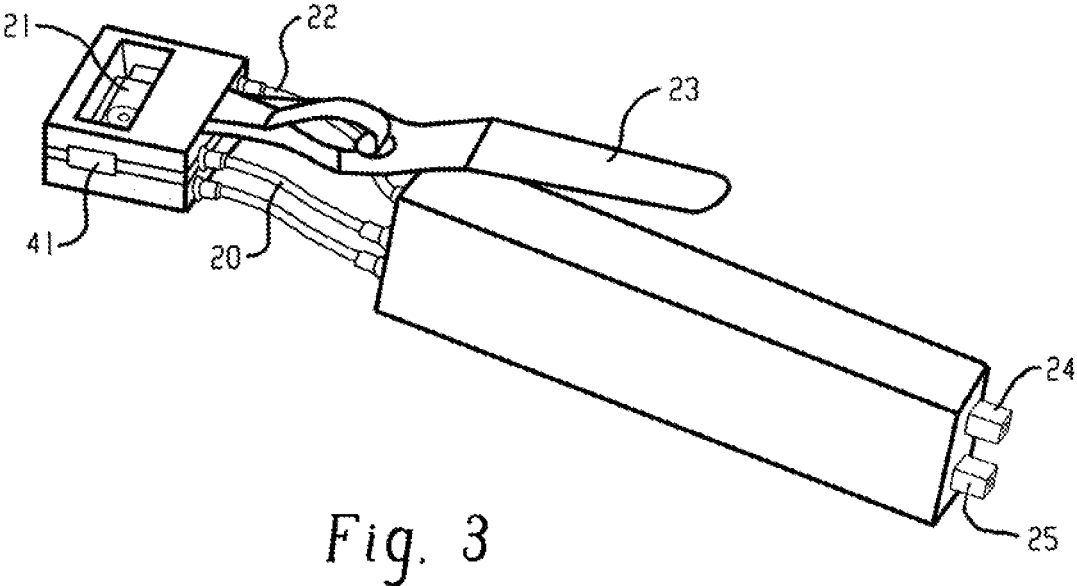
FIG. 3 is a perspective view of a leaf chamber module.
Figure 4:
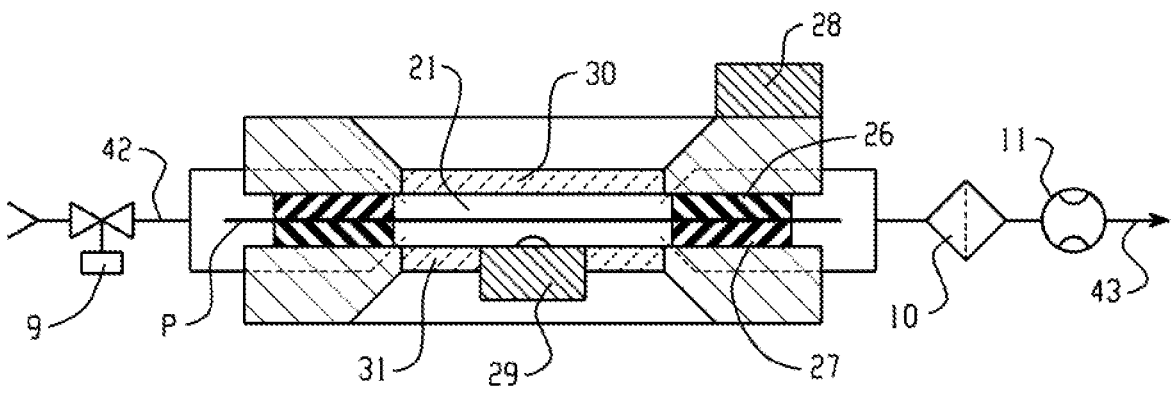
FIG. 4 is a thematic view of the leaf chamber module showing airflow into and out of the module.

The leaf chamber module 3 shown in FIG. 3 is a known type and is further shown schematically in FIG. 4. It has an inlet 24 for receiving air from the pump 2 and an outlet 25 for discharging air which has passed through a leaf chamber 21. The leaf chamber module 3 has an inlet pipe 20 to the leaf chamber 21 and an outlet pipe 22 from the leaf chamber. An operating lever 23 is provided to be hand operated to open the leaf chamber 21 for insertion of a plant leaf sample and is configured to close automatically under spring bias when the operating lever is released.

A sensor 41 is provided to sense when the leaf chamber 21 is open or closed, and is arranged to send appropriate signals to the system controller as to the open or closed status of the leaf chamber 21. This can ensure that, at least during a process of making measurements of plant leaf samples, the system controller 13 sends a signal to the solenoid valve 9 to open the valve and allow the flow of air from the pump to 2 to the inlet 24 of the leaf chamber module 3 only when the leaf chamber 21 closed.

FIG. 4 shows further details of the leaf chamber module 3. The module 3 has an upper seal 26 and a lower seal 27 which extend around the periphery of the leaf chamber 21. The leaf chamber 21 has an upper glass wall 30 and a lower glass wall 31 to assist an operator in positioning a plant leaf sample P in the leaf chamber. The leaf chamber 21 is shown in a closed condition with the plant leaf sample P gripped between the upper and lower seals such that a portion thereof extends across the leaf chamber. When the leaf chamber is opened by an operator pressing on the operating lever 23, the upper and lower seals separate to release the plant leaf sample P and allow insertion of another plant leaf sample.

A light intensity sensor 28 is provided to sense the intensity of light to which the plant leaf sample P is exposed in the leaf chamber. A leaf temperature sensor 29 is provided to sense the temperature of the plant leaf sample. Data from the light intensity sensor 28 and the leaf temperature sensor 29 is sent to the data processing and logging unit 14 in the form of signals.

A suitable gas analyzer used in the system described herein is model LI-850™ $H_2O/CO_2$ gas analyzer made by LI-COR, Inc.

Methods carried out using the apparatus of the embodiment will now be discussed.

Before starting measurements, the gravitational air pump 2 is filled by the pull handle 16 being pulled upwardly to expand the bellows 15 which then sucks ambient air into the bellows through the first one-way valve 6. For that operation, an air inlet to the air intake pipe 40 is set away from people and other potential sources of $CO_2/H_2O$. The dust filter 7 excludes from the air intake small particles that could damage the gas analyzer 4. Using the specially designed gravitational pump 2 gives several advantages over electrical gas pumps used in commercially available plant gas exchange systems: (1) it does not consume electricity, (2) it creates a constant air flow rate, i.e., avoids pulsations, (3) it collects ambient air with the same water vapor and $CO_2$ concentrations form the immediate neighborhood of analyzed plants, and (4) one measurement in the beginning of the measurements and one in the end is enough to know reference gas concentrations. A 2 liter volume of the pump is sufficient for analysis of 50-60 plant leaf samples each for six seconds at a flow rate of 5 ml s$^{-1}$. The pump may have a volume in a range of 1-3 liters, for example.

The leaf chamber 21 operates as an open system in which there is a constant air flow with a constant concentration of $CO_2$ and water vapor through the measuring chamber. The system measures changes in the concentration of $CO_2$ and $H_2O$ as a result of photosynthesis (decrease of $CO_2$) and transpiration (increase of $H_2O$) of the plant leaf sample in the chamber. Leaf temperature is measured with the sensor 29, which is preferably an infrared sensor, in the leaf chamber 21 and photosynthetically active radiation is measured with the sensor 28, which is preferably a quantum sensor. After the leaf chamber the gas is passed through the gas analyzer to measure changes in $CO_2$ and $H_2O$ concentrations, and values are stored and processed in the data processing and logging unit 14.

By knowing the gas flow rate, leaf temperature, changes in $CO_2$ and $H_2O$ concentrations and light; leaf rate of photosynthesis ($\mu$mol $CO_2$ m$^{-2}$ s$^{-1}$), transpiration (mmol $H_2O$ m$^{-2}$ s$^{-1}$) and some intracellular gas exchange parameters of leaf are calculated. These parameters are key characteristics for describing plant growth speed, possible stress status and can be used to make agro technological decisions (fertilizing, watering etc).

When the flow control valve is closed air flow from the bellows of the gravitational pump 2 is prevented, whereas, when the control valve is opened air flows through the leaf chamber and the air is passed through the gas analyzer. A control unit program can judge when the leaf chamber is open and exclude from its data processing the air that came to the system as a result of diffusion, when the leaf chamber was open. Changes in gas concentrations are small, after opening and closing the leaf chamber i.e., are caused only by the analyzed leaf, and this helps the gas analyzer to stabilize and measure faster.

The basic principle of the method is to set a uniform measurement time for collecting gas exchange data from a single plant leaf sample and to pool gas exchange values of several samples in the same plot of land within a short timeframe. The measurement time for collecting data from one plant leaf sample and number of samples for which data will be pooled can be adjusted by the experimenter. A minimal time for getting reliable values from one leaf is 5 seconds and a practical number of leaves measured within one measurement cycle is 20-50 leaves.

In the beginning of each measurement cycle air from the pump 2 is measured to get the reference $CO_2$ and $H_2O$ values, and after that measurements with plant leaves can start. As an example, in several tests in field conditions the exposure time of one plant leaf sample was set to 6 seconds and then it took approximately 6 minutes to measure photosynthesis and transpiration of 20 wheat leaves growing in a 2×5 m plot and measurement of 10 plots took an hour.

An example of a method for assessing gas exchange of plants will be described with reference to FIG. 5.

Initially, the leaf chamber 21 is closed and reference air from the pump is passed through the leaf chamber and to the gas analyzer 4, by virtue of the weight 19 exerting downward pressure on the bellows 15 providing a pumping pressure and the flow of reference air. The gas analyzer sends signals to the data processing and logging unit 14 which calculates the reference concentrations of $CO_2$ and $H_2O$, and stores that information.

The airflow from the pump 2 is stopped and the air pressure in the bellows 15 resists the downward pressure created by the weight 19. The leaf chamber 21 is opened and a first plant leaf sample is received therein. In this embodiment, a leaf is clamped between the seals around the periphery of the leaf chamber, so that a portion of the leaf forms the first plant leaf sample in the leaf chamber. Once the plant leaf sample is in position the leaf chamber is closed, and in response the leaf chamber module 3 sends a signal to the system controller 13, which in turn sends a signal to the solenoid valve 9 to open the valve. Air flow from the pump resumes and this continues for a predetermined testing period, in this case seven seconds. At the end of the predetermined period the system controller 13 sends a signal to the solenoid valve 9 to close the valve.

An indication is provided to the operator of the leaf chamber module 3 that the testing period for the sample is complete, so that the leaf chamber is then opened by the operator. The first plant leaf sample is removed and a second plant leaf sample is inserted in the leaf chamber. The operator closes the leaf chamber, and again the leaf chamber module 3 sends a signal to the system controller 13, which in turn sends a signal to the solenoid valve 9 to open the valve. Airflow from the pump again resumes and this continues for the same predetermined testing period, until the system controller 13 sends a signal to the solenoid valve 9 and the valve is closed.

During the period when the leaf chamber 21 is open for removal of the first plant leaf sample and insertion of the second plant leaf sample there is no airflow from the pump and so the air between the solenoid 9 and the leaf chamber, the air in the leaf chamber, and the air in the flow conduit 43 between the leaf chamber and the gas analyzer, is generally static. Some diffusion takes place between the inside of the leaf chamber and the surrounding ambient atmosphere. Once the leaf chamber is closed again the air captured therein is a mixture of air affected by the first plant leaf sample and ambient air. With the resumption of airflow through the system, this mixed air later reaches the gas analyzer.

The exposure of the first plant leaf sample to light in the leaf chamber during the first predetermined test period (seven seconds in this example) generates a first test air sample. This flows out of the leaf chamber with a leading part in the flow direction, an intermediate part upstream of the leading part, and a trailing part upstream of the intermediate part. Upstream of this there is the mixture of air described above. As flow continues along the flow conduit 43 out of the leaf chamber 21 and towards the gas analyzer 4, the mixture is followed by a second test air sample generated by the second plant leaf sample. The second test air sample also has a leading part in the flow direction, an intermediate part upstream of the leading part, and a trailing part upstream of the intermediate part.

The first and second test air samples form an integrated gas stream, in that they flow together in a row and at the same rate, including if the flow stops, such as for example when the leaf chamber is opened. Thus, the integrated gas stream flows or stops in an integrated manner. This is similar to the carriages of a train, which move together or stop in unison. The first and second test air samples flow in parallel and one after the other into the gas analyzer from the leaf chamber.

As described in relation to this embodiment, the integrated gas stream also includes an air mixture corresponding to the time when the leaf chamber is open. When the integrated gas stream stops flowing, for example at a time when the leaf chamber is opened to remove the second plant leaf sample and insert a third plant leaf sample, the first and second test air samples stop together with the air mixture upstream of the first test air sample and downstream of the second test air sample.

Figure 5:
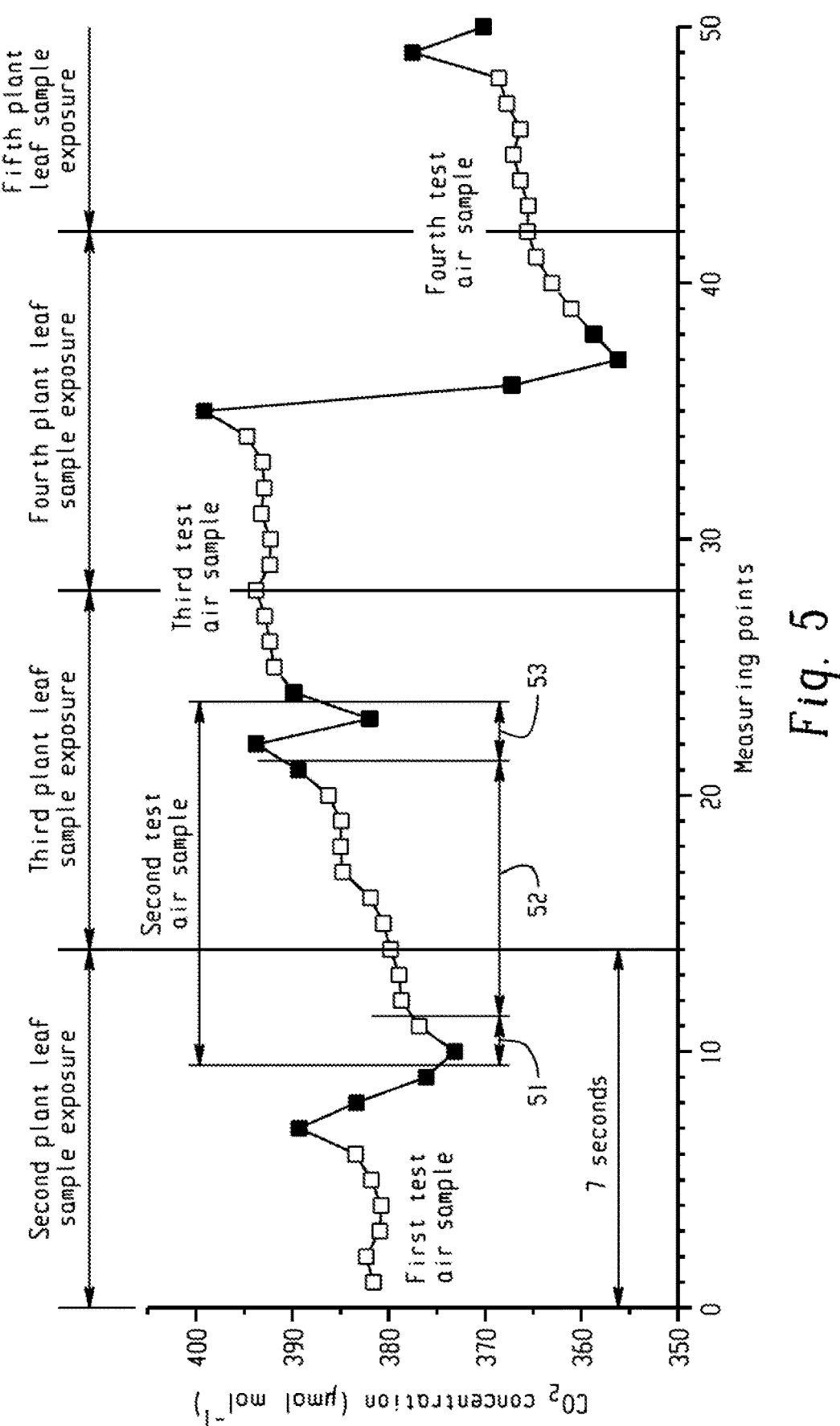
FIG. 5 is a graph showing the results of an experiment with the apparatus.

FIG. 5 is a graph showing signal points representing the concentration of $CO_2$ at timewise spaced measuring points, as measured by the gas analyzer and sent as signals to the processing and logging unit 14. The graph shows the concentrations measured for second, third and fourth plant leaf samples, as indicated. In this example, each plant leaf sample was exposed for a testing period of seven seconds, and each test air sample generated by the exposure flowed along the flow conduit to the gas analyzer.

The signal data points each correspond to a measurement taken over 0.5 seconds, so that there are 14 signal data points for each plant leaf sample for the seven second test. The graph shows signal data points as hollow squares and filled in squares. Considering the second test air sample, indicated as "Second test air sample" in the graph, this has a leading part 51 consisting of two filled in squares, an intermediate part 52 consisting of 10 hollow squares, and a trailing part 53 consisting of two filled in squares.

The signal data points of the intermediate part are used by the data processing and logging unit 14 to determine the $CO_2$ concentration measured for the second plant leaf sample. This is because the leading part 51 is adjacent to mixed air in the flow conduit 43 from the leaf chamber to the gas analyzer, corresponding to the time when the chamber was opened to remove the first plant leaf sample and insert the second plant leaf sample. During this open time ambient air diffuses into the leaf chamber, so that when the chamber is closed again it contains a mixture of air from the first plant leaf sample test and ambient air. By using the intermediate part 52 of the second test air sample, gas concentrations in the leading part 51 influenced by the mixture of air between the first and second test air samples are disregarded. Similarly, by using the intermediate part 52 of the second test air sample, gas concentrations in the trailing part 53 influenced by the mixture of air between the second and third test air samples are disregarded.

The signal data points of the leading part 51 and the trailing part 53 of the second test sample are disregarded by the data processing and logging unit 14. The same applies to the other test air samples.

The graph in FIG. 5 shows the signal points as measured in the gas analyzer as the air flows therethrough. It will be seen from the upper region of the graph that whilst the second test air sample flows through the gas analyzer, the third plant leaf sample is being exposed in the leaf chamber to air from the pump. The same applies to the other test air samples and plant leaf sample exposures.

The graph shows the results for measuring $CO_2$ and similar measurements are carried out for $H_2O$.

In the experiment the results of which are shown in FIG. 5, it will be seen that each plant leaf sample had different levels of photosynthesis. The fourth plant leaf sample had the highest photosynthesis, producing signal points with the lowest $CO_2$ concentrations, and the third plant leaf sample had the smallest photosynthesis. The first and second plant leaf samples had approximately the same photosynthesis as each other.

The data processing and logging unit 14 receives the signal points for the gas concentrations from the gas analyzer. Previously, signal points for the gas concentrations from the reference air were measured by the gas analyzer, passed to the data processing and logging unit 14, and stored in a memory thereof. The data processing and logging unit 14 calculates the change in $CO_2$ and $H_2O$ gas concentrations compared to the concentrations of those gases in the reference air. These changes represent the photosynthesis (decrease in $CO_2$) and transpiration (increase in $H_2O$) activity of each plant leaf sample. Based on the gas concentration measurements of plural plant leaf samples, the data processing and logging unit 14 calculates average values for photosynthetic activity and water transpiration. The data processing and logging unit 14 generates a combined gas exchange analysis for the plural leaf samples, this analysis being derived from the sets of signal points produced by the gas analyzer for the plural plant leaf samples.

Such a measurement procedure makes it possible to analyze a large number of leaves in a relatively short timeframe and gives the average values for photosynthetic activity and water transpiration, which quite correctly reflects the physiological status of plants in the community. Moreover, short exposures (5-6 seconds) provides this data corresponding to the real situation in the field, since during this time the "chamber effect" is minimal. No other commercially available gas exchange system allows such speed in gas exchange data collection.

The apparatus and method of the embodiment allow assessment of the physiological status of plant communities in the field and this information can be used in agro technological decision-making processes or for selecting plant lines with improved photosynthetic production and efficient water-use.

It will be seen that in this specification there is described a novel scheme for obtaining gasometric data from plant leaf samples. The apparatus and applied methodology are based on fast measurements of photosynthesis and transpiration of a large number of leaves according to a principle of "many samples—one measurement". Such a method is revolutionary and allows the measurement of the physiological parameters of entire plant communities. The principle of this method involves integration of the measured samples by summing up individual short measurements. Such a measurement principle allows the analysis of one plant leaf sample within a very short exposure time and enables the collection of data from a large number of leaves within a few minutes.

Considering the daily dynamics of the environment, as well as the complex structure of plant communities in the field, the system of the embodiments described herein is advantageous because it can provide gas exchange data for several hundreds of leaves in one day. The portable apparatus enables in situ measurements of photosynthesis of plural plant leaf samples, for example hundreds of leaves, under natural dynamic field conditions and at different layers within the canopy is required.

The invention claimed is:

1. A measuring apparatus for assessing gas exchange of plants, comprising a leaf chamber for receiving therein a plant leaf sample to be tested, a pump communicating with the leaf chamber for supplying air thereto, an analyzer communicating with the leaf chamber for receiving air therefrom and for analyzing the air received, wherein the pump is configured to be filled with a single charge of air and to supply plural doses of air from that single charge each for sequentially testing a respective plant leaf sample of a plurality of plant leaf samples.

2. The measuring apparatus as claimed in claim 1, wherein the pump is a bellows pump comprising a bellows and a weight for applying pressure to the bellows to discharge air.

3. The measuring apparatus as claimed in claim 1, further comprising a first one-way valve in an inlet path allowing the pump to be filled and a second one-way valve in an outlet path allowing discharge of air from the pump.

4. The measuring apparatus as claimed in claim 1, further comprising a flow control valve upstream of the leaf chamber for controlling flow of air into the leaf chamber.

5. A method for assessing gas exchange of plants, comprising receiving in the gas analyzer of claim 1 a plurality of test air samples from a leaf chamber each corresponding to a respective one of a plurality of plant leaf samples received separately and in sequence in the leaf chamber while being exposed to light to form the plurality of test air samples, the plurality of test air samples being received in sequence in the gas analyzer, and the gas analyzer analyzing the plurality of test air samples in the sequence.

6. The method as claimed in claim 5, further comprising receiving analysis data from the gas analyzer, processing the analysis data to produce a test result for each of the plant leaf samples, and combining the test results for the plant leaf samples to generate an average test result for the plant leaf samples.

7. The method as claimed in claim 6, wherein the analysis data received from the gas analyzer comprises a plurality of sets of signal points sequenced over time, each set of signal points corresponding to a respective test air sample of the plurality thereof.

8. The method as claimed in claim 7, wherein each of the test air samples received in the gas analyzer comprises a leading part in the flow direction, an intermediate part upstream of the leading part, and a trailing part upstream of the intermediate part, and the method comprising processing the signal points of the sets thereof which correspond to the intermediate parts of the test air samples to produce said test result for each of the plurality of plant leaf samples.

9. The method as claimed in claim 5, further comprising allowing an air flow into the leaf chamber to form the test air samples.

10. The method as claimed in claim 5, further comprising allowing reference air to flow through the leaf chamber when empty, before a first of the plurality of plant leaf samples has been received in the leaf chamber, and the gas analyzer analyzing the reference air.

11. The method as claimed in claim 10, wherein the reference air flow is obtained from a single source of reference air, and wherein air flow into the leaf chamber to form the test air samples is also obtained from the single source of reference air.

12. The method as claimed in claim 10, wherein the reference air is unprocessed ambient air.

13. The method as claimed in claim 5, wherein said plurality of test air samples comprises at least 10 test air samples.

14. The method as claimed in claim 5, wherein each plant leaf sample is received in the leaf chamber for a period of 15 seconds or less.

15. An apparatus for assessing gas exchange of plants, comprising a leaf chamber configured to receive a plurality of plant leaf samples separately and sequentially therein and to expose the plant leaf samples to light while passing air through the leaf chamber to form a corresponding plurality of test air samples, the leaf chamber being openable for removal of one of the plurality of plant leaf samples therefrom and for receiving therein a next plant leaf sample of the plurality thereof, a gas analyzer configured to receive from the leaf chamber the plurality of test air samples in sequence and to analyze the plurality of test air samples in the sequence, and a data processor configured to receive analysis data from the gas analyzer, to process the analysis data to produce a test result for each of the plant leaf samples, and to combine the test results for the plant leaf samples to generate an average test result for the plant leaf samples.

16. The apparatus as claimed in claim 15, wherein the gas analyzer is configured to analyze the gas stream to produce a plurality of sets of signal points sequenced over time, each set of signal points corresponding to a respective test air sample of the plurality thereof.

17. The apparatus as claimed in claim 16, wherein each of the test air samples received in the gas analyzer comprises a leading part in the flow direction, an intermediate part upstream of the leading part, and a trailing part upstream of the intermediate part, and the data processor being configured to process the signal points of the sets thereof which correspond to the intermediate parts of the test air samples to produce said test result for each of the plurality of plant leaf samples.

18. The apparatus as claimed in claim 15, further comprising a flow control valve for allowing an air flow into the leaf chamber to form the test air samples, and/or comprising a sensor for sensing when the leaf chamber is open or closed.

19. The apparatus as claimed in claim 15, further comprising a pump configured to be filled with a single charge of air and sequentially to supply plural doses of air from the single charge each for passing to the leaf chamber.

* * * * *